United States Patent
McGilvery et al.

(10) Patent No.: US 9,757,066 B2
(45) Date of Patent: *Sep. 12, 2017

(54) METRICS ASSESSMENT SYSTEM FOR HEALTH, FITNESS AND LIFESTYLE BEHAVIORAL MANAGEMENT

(71) Applicant: Fat Statz LLC, Laguna Niguel, CA (US)

(72) Inventors: Justin McGilvery, Laguna Niguel, CA (US); Dale E. Mitbo, Orange, CA (US)

(73) Assignee: Fat Statz LLC, Laguna Niguel, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/401,922

(22) Filed: Jan. 9, 2017

(65) Prior Publication Data

US 2017/0112432 A1   Apr. 27, 2017

Related U.S. Application Data

(63) Continuation of application No. 15/199,513, filed on Jun. 30, 2016, now abandoned, which is a
(Continued)

(51) Int. Cl.
*A61B 5/00* (2006.01)
*G09B 19/00* (2006.01)
(Continued)

(52) U.S. Cl.
CPC ............ *A61B 5/486* (2013.01); *A61B 5/0002* (2013.01); *A61B 5/024* (2013.01); *A61B 5/112* (2013.01); *A61B 5/4806* (2013.01); *A61B 5/4866* (2013.01); *A61B 5/4872* (2013.01); *G06F 19/345* (2013.01); *G06F 19/3418* (2013.01); *G06F 19/3475* (2013.01); *G06F 19/3487* (2013.01); *G06F 19/363* (2013.01); *G06Q 50/22* (2013.01); *G06Q 50/24* (2013.01); *G09B 5/02* (2013.01); *G09B 7/06* (2013.01); *G09B 19/0038* (2013.01); *G09B 19/0092* (2013.01)

(58) Field of Classification Search
CPC .... G06Q 50/22; G06Q 50/24; G06F 19/3475; G06F 19/3487; G06F 19/345; G06F 19/363
USPC ........................................................ 434/127
See application file for complete search history.

(56) References Cited

U.S. PATENT DOCUMENTS 7,647,234 B1   1/2010  Ruderman et al.
7,953,613 B2   5/2011  Gizewski
(Continued)

OTHER PUBLICATIONS

Adult BMI. <URL:http://www.cdc.gov/healthyweight/assessing/bmi/adult_bmi/> [Retrieved Jul. 27, 2015 1:53:09 PM from US Center for Disease Control website, www.cdc.gov].
(Continued)

*Primary Examiner* — Nikolai A Gishnock
(74) *Attorney, Agent, or Firm* — Knobbe Martens Olson & Bear LLP

(57) ABSTRACT

A software and hardware system is described that enables effective lifestyle management by providing a dynamic assessment of a user's physical and behavioral metrics via a high feedback ratio interface.

17 Claims, 15 Drawing Sheets

Related U.S. Application Data continuation of application No. 12/717,811, filed on Mar. 4, 2010, now Pat. No. 9,400,872.

(60) Provisional application No. 61/157,856, filed on Mar. 5, 2009.

(51) Int. Cl.
| | |
|---|---|
| *G09B 5/02* | (2006.01) |
| *G09B 7/06* | (2006.01) |
| *A61B 5/024* | (2006.01) |
| *A61B 5/11* | (2006.01) |
| *G06F 19/00* | (2011.01) |
| *G06Q 50/22* | (2012.01) |
| *G06Q 50/24* | (2012.01) |

(56) References Cited

U.S. PATENT DOCUMENTS

| | | | |
|---|---|---|---|
| 7,959,567 B2 * | 6/2011 | Stivoric | A61B 5/411 |
| | | | 128/921 |
| 7,974,881 B2 * | 7/2011 | Culver | G06F 19/3475 |
| | | | 426/72 |
| 7,988,628 B2 | 8/2011 | Bagan | |
| 8,219,414 B2 | 7/2012 | Bessette et al. | |
| 9,400,872 B2 * | 7/2016 | McGilvery | G06Q 50/22 |
| | | | 434/127 |
| 2001/0032098 A1 | 10/2001 | Kulkarni | |
| 2001/0041845 A1 | 11/2001 | Kim | |
| 2002/0011923 A1 | 1/2002 | Cunningham et al. | |
| 2002/0028995 A1 | 3/2002 | Mault | |
| 2002/0049482 A1 | 4/2002 | Fabian et al. | |
| 2002/0066602 A1 | 6/2002 | Bliss et al. | |
| 2002/0087054 A1 | 7/2002 | Lin et al. | |
| 2002/0128914 A1 | 9/2002 | Sansone | |
| 2002/0139588 A1 | 10/2002 | Brandt | |
| 2003/0024745 A1 | 2/2003 | Huitt et al. | |
| 2003/0055461 A1 | 3/2003 | Girouard et al. | |
| 2003/0059747 A1 | 3/2003 | Yoshida et al. | |
| 2003/0208108 A1 | 11/2003 | Shewmake et al. | |
| 2003/0208113 A1 | 11/2003 | Mault et al. | |
| 2003/0208409 A1 | 11/2003 | Mault | |
| 2003/0212579 A1 | 11/2003 | Brown et al. | |
| 2003/0229514 A2 | 12/2003 | Brown | |
| 2004/0044560 A1 | 3/2004 | Giglio et al. | |
| 2004/0131997 A1 | 7/2004 | McGuire et al. | |
| 2004/0148127 A1 | 7/2004 | Kriger | |
| 2005/0006152 A1 | 1/2005 | Eldeiry | |
| 2005/0038326 A1 | 2/2005 | Mathur | |
| 2005/0228692 A1 | 10/2005 | Hodgdon | |
| 2005/0234742 A1 | 10/2005 | Hodgdon | |
| 2006/0129432 A1 | 6/2006 | Choi et al. | |
| 2007/0026365 A1 | 2/2007 | Friedrich et al. | |
| 2007/0100666 A1 | 5/2007 | Stivoric et al. | |
| 2008/0004904 A1 | 1/2008 | Tran | |
| 2008/0162352 A1 | 7/2008 | Gizewski | |
| 2008/0275309 A1 | 11/2008 | Stivoric et al. | |
| 2009/0326981 A1 | 12/2009 | Karkanias et al. | |
| 2010/0076787 A1 | 3/2010 | Naylor et al. | |
| 2012/0010897 A1 | 1/2012 | Bagan | |
| 2012/0303381 A1 | 11/2012 | Bessette | |

OTHER PUBLICATIONS http://www.accufitness.com, accessed Apr. 18, 2017.

* cited by examiner

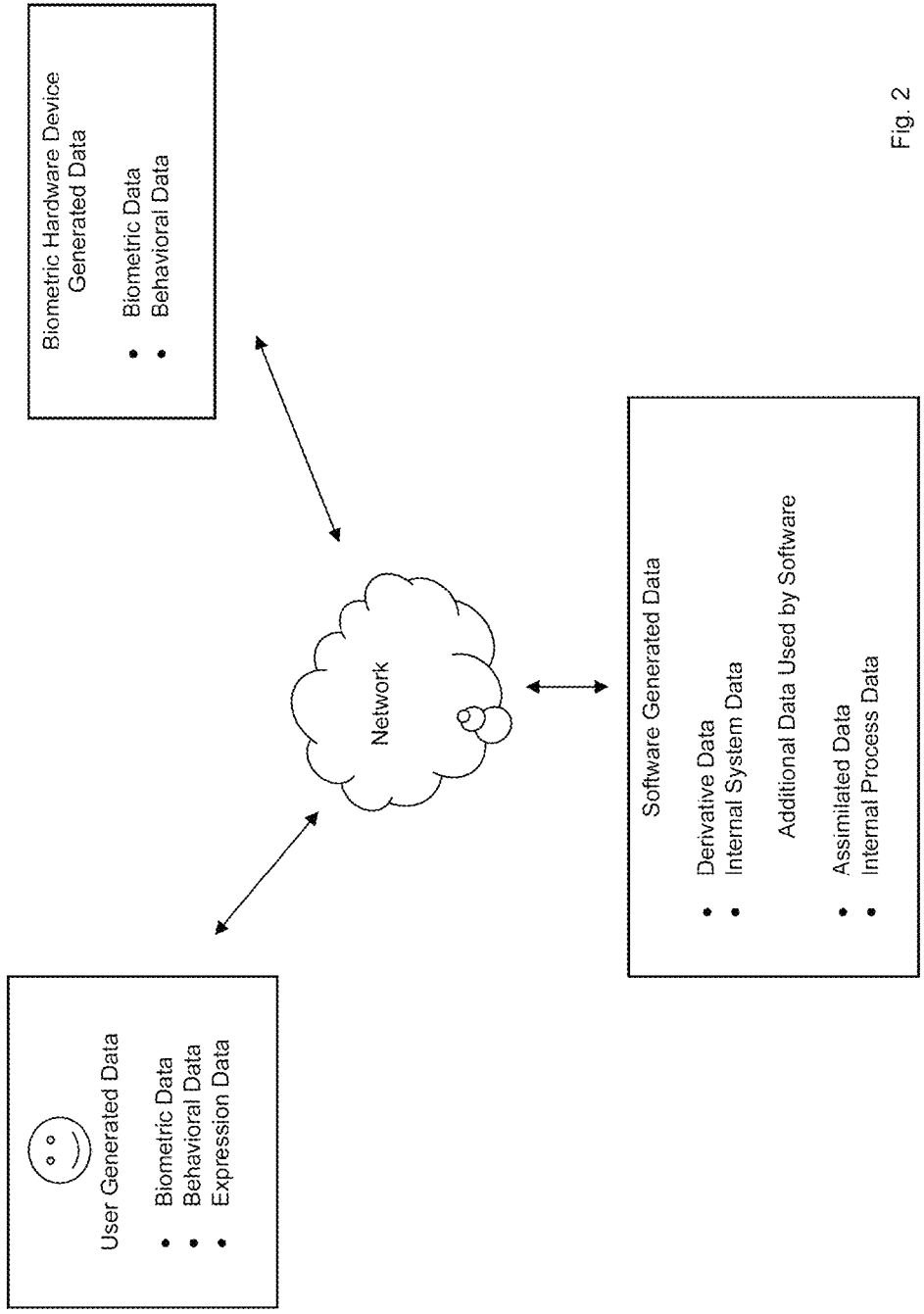

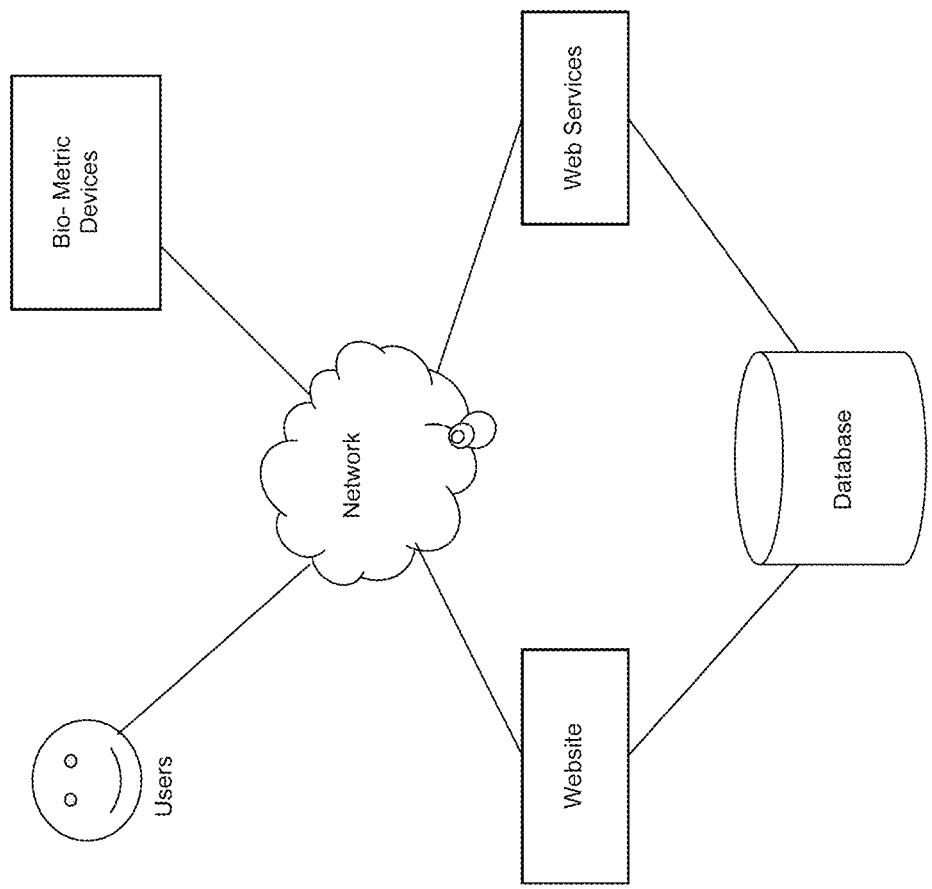

GETTING STARTED - GOAL

Define Your Goal

Fig. 6A

Schedule Your Exercise

Tip: Make A Realistic Commitment. How much exercise time can you commit to? It's okay to start slowly. Simple activities, like walking, count! National Institute of Health minimum recommendation: 30 minutes, three to four times per week

| Sunday | Monday | Tuesday | Wednesday | Thursday | Friday | Saturday |
|---|---|---|---|---|---|---|
| ⦿ Rest<br>○ Exercise | ○ Rest<br>⦿ Exercise [45 min ▷] | ○ Rest<br>⦿ Exercise [30 min ▷] | ⦿ Rest<br>○ Exercise | ⦿ Rest<br>○ Exercise [30 min ▷] | ○ Rest<br>⦿ Exercise [20 min ▷] | ⦿ Rest<br>○ Exercise |

Total minutes per week [125]

When done, click: [Continue]

FIG. 6B

GETTING STARTED – MOTIVATION

Motivation

● Carrots or Sticks
How do you motivate yourself?

○ Promise myself a reward
Rewards give me a good reason to work toward a goal. I feel rewards make goals easier to achieve.

● Focus on change
I have a goal because something needs changing. I am motivated to change it because I don't want things to stay as they are.

● Burst or Steady
What's your energy level?

○ Burst of energy
I like starting something new with a burst of energy. I feel a lot of momentum will carry me forward.

● Steady Energy
I usually start new things with an even energy level that I can maintain. I want to save energy for the long haul.

● Extrovert or Introvert
How are you engaged?

○ Reach out to others
I like interaction with others when I'm striving for goals. Friends make the journey fun, and knowing they're watching motivates me.

● Keep to myself
I'm usually private about my goals and don't really want friends watching me. I keep motivated by thinking about the promises I've made to myself.

● Sensory or Numerical
How do you measure progress?

● Feel the difference
I usually wait to measure my progress until I can feel a difference. I'll step on a scale when my pants fit better.

○ See the numbers
I like to measure my progress often. If I don't measure my progress I can't be sure I'm improving.

GETTING STARTED – OBSTACLES

Obstacles

Tip: Select the behaviors below that best describe reasons that have prevented you from achieving a similar goal in the past.

- ☑ I got bored, lost interest
- ☑ I gave into cravings
- ☐ I missed a day and fell off my plan
- ☐ Social pressures made it too hard
- ☐ Other

- ☑ I got lonely doing it alone
- ☑ I didn't have enough time
- ☑ I don't know how to exercise properly

- ☐ I didn't have a plan
- ☑ I was just lazy
- ☐ I got injured

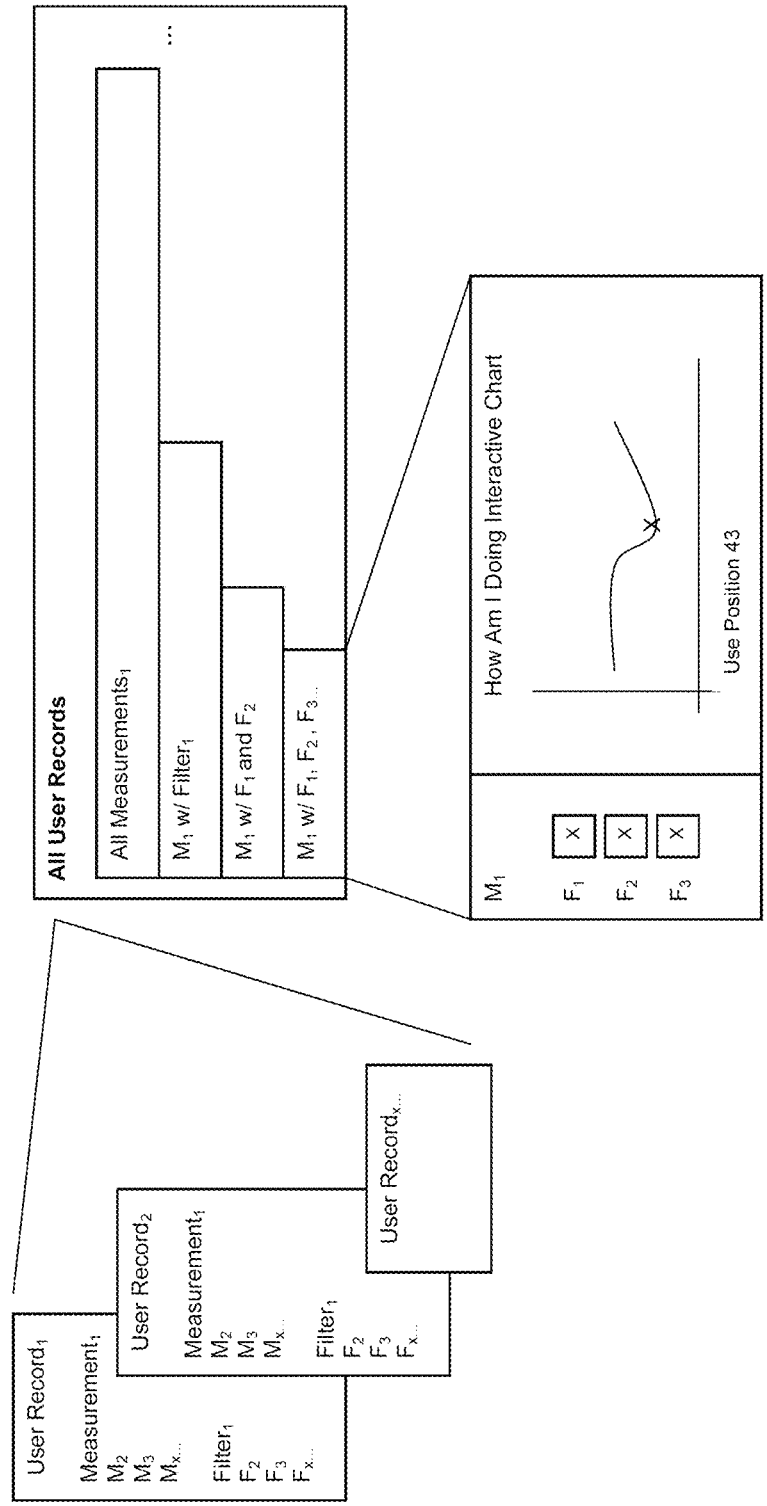

METRICS ASSESSMENT SYSTEM FOR HEALTH, FITNESS AND LIFESTYLE BEHAVIORAL MANAGEMENT

RELATED APPLICATIONS

This present application is a continuation of U.S. non-Provisional Application Ser. No. 15/199,513, filed Jun. 30, 2016, which is a continuation of U.S. Non-Provisional Application Ser. No. 12/717,811, filed Mar. 4, 2010, now U.S. Pat. No. 9,400,872, issued Jul. 26, 2016, which claims priority to U.S. Provisional Application No. 61/157,856, filed Mar. 5, 2009. Each of these applications are incorporated by reference herein in their entireties.

BACKGROUND OF THE INVENTION

Field of the Invention

The present invention relates generally to health, fitness, and lifestyle management, and more specifically to a software and hardware system which enables effective lifestyle management by providing a dynamic assessment of a user's physical and behavioral metrics via a high feedback ratio interface.

Description of the Related Art

In the U.S., diet, exercise and personal health improvement markets exceed $60 billion annually; yet, two thirds of adults are overweight. Links between obesity and numerous serious and fatal health conditions are well documented. Lost worker productivity and increased health care costs in America due to obesity exceed $100 billion annually. Being obese is unhealthy, expensive and diminishes one's quality of life. These sobering realities, as well as social and personal pressures, however, are apparently not effective enough drivers for most people to achieve a healthy weight. Obesity rates in America and around the developed world continue to rise at an alarming pace. A schism exists between what people want, or even need, and what they achieve.

Although 95% of diets reportedly fail, the 5% who succeed at losing weight represent the entirety of the social, economic and physiological demographic spectrum. What, then, is the primary reason for this schism? The key differentiator between those who succeed and fail is motivation and behavior management. Motivation fuels behavior and results follow behavior. The schism, then, is a failure of behavior management.

A well-known key to weight control is a daily caloric balance—consume only as many calories in a day as are burned. That simple equation, however, and corresponding behavior is simply unattainable for many people. Why? Because the effort-to-reward mechanism is ineffective for too many people.

Motivation is unsustainable in an ineffective effort-to-reward mechanism. An effective effort-to-reward mechanism can sustain motivation and enable effective behavior management. Effective effort-to-reward mechanisms meet necessary thresholds and balance of the following four criteria:

1. Temporal—a reward must be timely enough to the effort to be an effective motivator. Optimally, the reward would occur during the effort or immediately following.
2. Association—an effort and reward must be tangibly related to one another to be an effective motivator. Optimally, the effort and reward are viscerally related, an innately understood link.
3. Assimilation—a reward must have meaning and value to the subject to be an effective motivator.
4. Ratio—a reward-to-effort ratio must meet a minimum threshold to be an effective motivator. The higher the ratio of reward to effort the more effective the motivation.

It is important to note that 'necessary thresholds' vary from person to person. One size does not fit all. A system or method must be flexible to allow individual discovery of their own effective motivational threshold. In a fully realized healthy lifestyle, 'exercise' and 'eating right' become rewards themselves.

Existing methods or systems to heighten people's motivation and enable behavior management to achieve health, fitness and lifestyle goals include: weight-loss counseling, pre-prepared and portioned meals, peer-to-peer support groups, fitness groups and clubs, health challenges, hypnosis and many others. Many of these methods and systems have been in existence for years, even decades, yet obesity rates have nearly doubled in the past thirty years. For many people, current methods and systems fail to satisfy all four requirements of an effective effort-to-reward mechanism.

Most lifestyle goals cannot be achieved in a single action; they are a process, achieved over time. If the action and behavior itself is not a reward mechanism for the individual, then additional feedback and reward mechanisms are necessary.

Prior art methods or systems that attempt temporally effective reward mechanisms include data tracking websites or websites associated with personal biometric devices. The data feedback on such sites is often focused on a single metric, which is narrow and minimally informative.

Weight-loss support group sites have a marginally better feedback ratio for posted comments or messages; users can receive several replies for each message. The relationship between the feedback/reward and the user's overall goal in these cases, however, is marginalized. If the user's overall goal is to lose weight, for example, how direct of a reward to that effort is this feedback? The reward of support messages is more closely related to the behavior of message exchanging itself, and only tangentially related to losing weight. It is a step removed from the efforts and behaviors of actually losing weight.

A user needs a personal connection or meaning to the feedback/reward to be effective. Too often, user profiling is not sufficiently varied or personalized. Meaningful feedback, therefore, is limited and contributes to low effort-to-reward feedback ratios.

In existing systems, the desired goal is often a number, a fixed measurement, of what is considered healthy for someone with the user's attributes. This number, this goal measurement, is historically a very poor motivator. People have been told what they are supposed to weigh many times already. Familiarity with a number is not the same as a relationship or meaning.

SUMMARY OF THE INVENTION

What is needed is a new set of assessment metrics that are fresh, motivating, and meaningful. The present invention provides methods and systems of motivation and behavior management that provides a user with a novel assessment with an effort-to-reward mechanism that is (1) temporal, (2) tangible, (3) personally meaningful, and (4) has a much greater feedback ratio that is far more effective than existing weight-loss, fitness and lifestyle programs.

To enable effective health, fitness and lifestyle behavior management, a software and hardware system has been developed that provides immediate, meaningful and engaging feedback for physical and behavioral metrics by providing a dynamic assessment of these metrics via a high feedback ratio interface. The system simultaneously meets the requirements of all four effort-to-reward feedback mechanisms—temporal, association, assimilation, and ratio—of an effective behavior management tool.

The hardware and software system is designed to optimize data collection, organization and display. Hardware components include integrated biometric devices, such as scales, that make data collection automatic and comprehensive. Data is stored and organized on computer servers. User assessments and data display are conveniently accessible from Internet-enabled devices.

A powerful system of metrics and filters allows for a simultaneously broad and deep user assessment spectrum. Motivational and obstacle profile typing provide a greater variety of data nodes in member records creating flexibility. New assessment metrics, including positions and rankings, utilize dynamic reference data sets that can be filtered to more and more closely resemble any particular user. User interactivity with the data enriches the user experience and provides more meaningful data feedback, and is a key to the effort-to-reward mechanism. Feedback based on cross referencing various metrics simultaneously can assist in users refining their behaviors to be more effective.

Users complete their profile by defining their goal, exercise and nutrition schedule, motivational and obstacle data, and other system preferences. Each of these data points is an additional data node for organizing feedback. Upon completing their profile, users record their activities on a daily basis and their physical measurements periodically. From time to time, users may participate in health and fitness challenges, competitions or other data organizational schemes. Physical measurements may be recorded manually or automatically via an integrated biometric device. Immediately following data entry, users access one of several dynamic high feedback ratio interfaces. These interfaces allow the user to obtain an assessment of physical metrics, such as weight and body fat percentage, or behavioral metrics, such as login frequency and mood. A variety of metric assessments are available. Assessment feedback is dynamic, in that, the active reference data set changes with overall system usage in nearly live terms.

Rankings and position assessments offer viscerally understood answers to "how am I doing?" questions. Via various screens, users can be ranked or positioned, on a percentile scale of 1-1 00, against other profiles in the active reference data set. The active reference data set is flexible; it can be filtered at the user's whim in real time.

The dynamic and flexible ranking and position assessments features satisfy the criteria for an effective behavior management system:

Temporal Assessment feedback rewards immediately follow user data entry.

Association The behavior of entering data and data assessment feedback are directly related. Users, in effect, take a "BodySpex measurement" to find out how they're doing.

Assimilation Ranking and positions on a scale of I-100 are innately easy to grasp. Filtering allows for meaningful reference data sets.

Ratio Multiple metrics and filters options provide users with a feedback interface that is very high-ratio.

This system is a positive feedback loop. The very act of accessing the database to see a user's rank and/or position adds more data to the database. A user enters his or her data to find out where he/she ranks, thus increasing the data pool for the next user. The increased data pool is more informative, more valuable, and encourages the next user to see where he or she ranks.

BRIEF DESCRIPTION OF THE DRAWINGS

The present invention is illustrated by way of example and not limited m the accompanying figures in which:

FIG. 2 shows a flow diagram of data types in a hardware and software behavioral management system. User generated data, biometric hardware device generated data, and software generated data flow over a network.

FIG. 4 shows a block diagram of the System Architecture, which illustrates the relationships between users, biometric devices, the website, web services, and the database.

FIG. 6A shows an exemplary webpage for a user defining their goal in the getting started sequence. Users define their goal, assign their metric and target measure measurement. This goal is related to personal goal reasons and goal rewards creating additional data nodes for feedback.

FIG. 6B shows an exemplary webpage for a user scheduling their exercise in the getting started sequence. Users assign each day of the week for rest or exercise. For exercise days, the user declares how many minutes he/she plans to engage in some form of exercise. In some embodiments, the user can select from a menu of specific exercises or fully defined exercise plans. These are additional data nodes for feedback.

FIG. 6D shows an exemplary webpage for a user completing their motivational profile in the getting started sequence. A user is presented with four questions with an A or B answer which most closely reflects their motivational profile. This feature creates sixteen distinct motivational profiles and each user is flagged for one and only one. This is an additional data node for feedback.

FIG. 6E shows an exemplary webpage for a user completing their obstacle profile in the getting started sequence. A user is presented with a list of obstacle statements which are selected as applicable to reflect the user's historical obstacles to achieving their goal. This feature is organized to create sixteen distinct obstacle profiles and each user is flagged for one and only one. This is an additional data node for feedback.

FIG. 7 shows a diagram of how user data is accessible and flexible via the interactive chart. User records include all personal physical and behavioral measurements as well as other data typing used for filters. All user records are stored and organized together and can be accessed via the feedback interfaces to find measurement data counts given any combination of filters.

DETAILED DESCRIPTION OF THE PREFERRED EMBODIMENT

Figure 1:
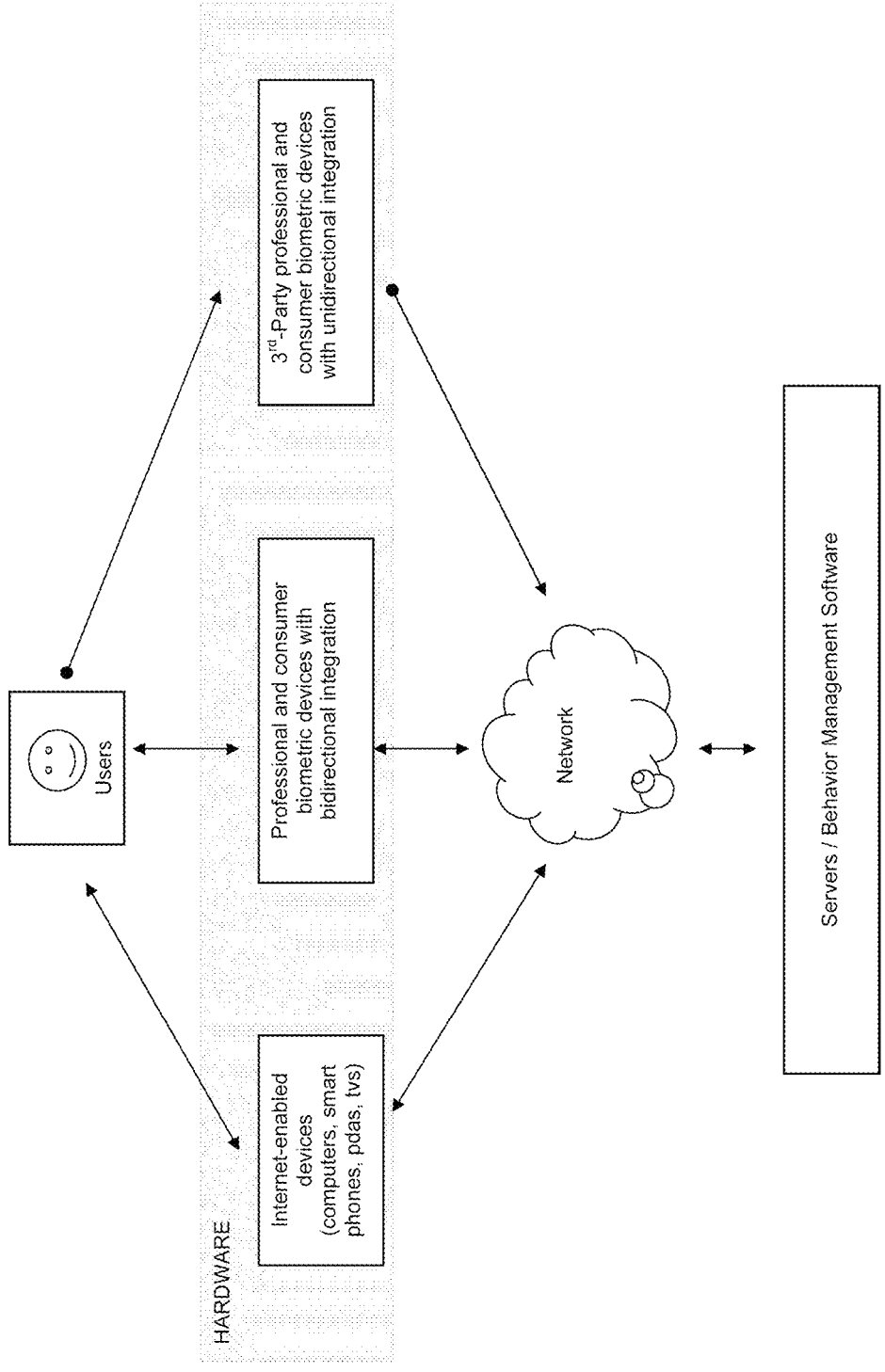
FIG. 1 shows a block diagram of components of a hardware and software behavioral management system. Users are connected to the behavior management software via hardware and a network. Hardware includes Internet-enabled devices, professional and consumer biometric devices with bidirectional integration and third party professional and consumer biometric devices with unidirectional integration.
Figure 1A:
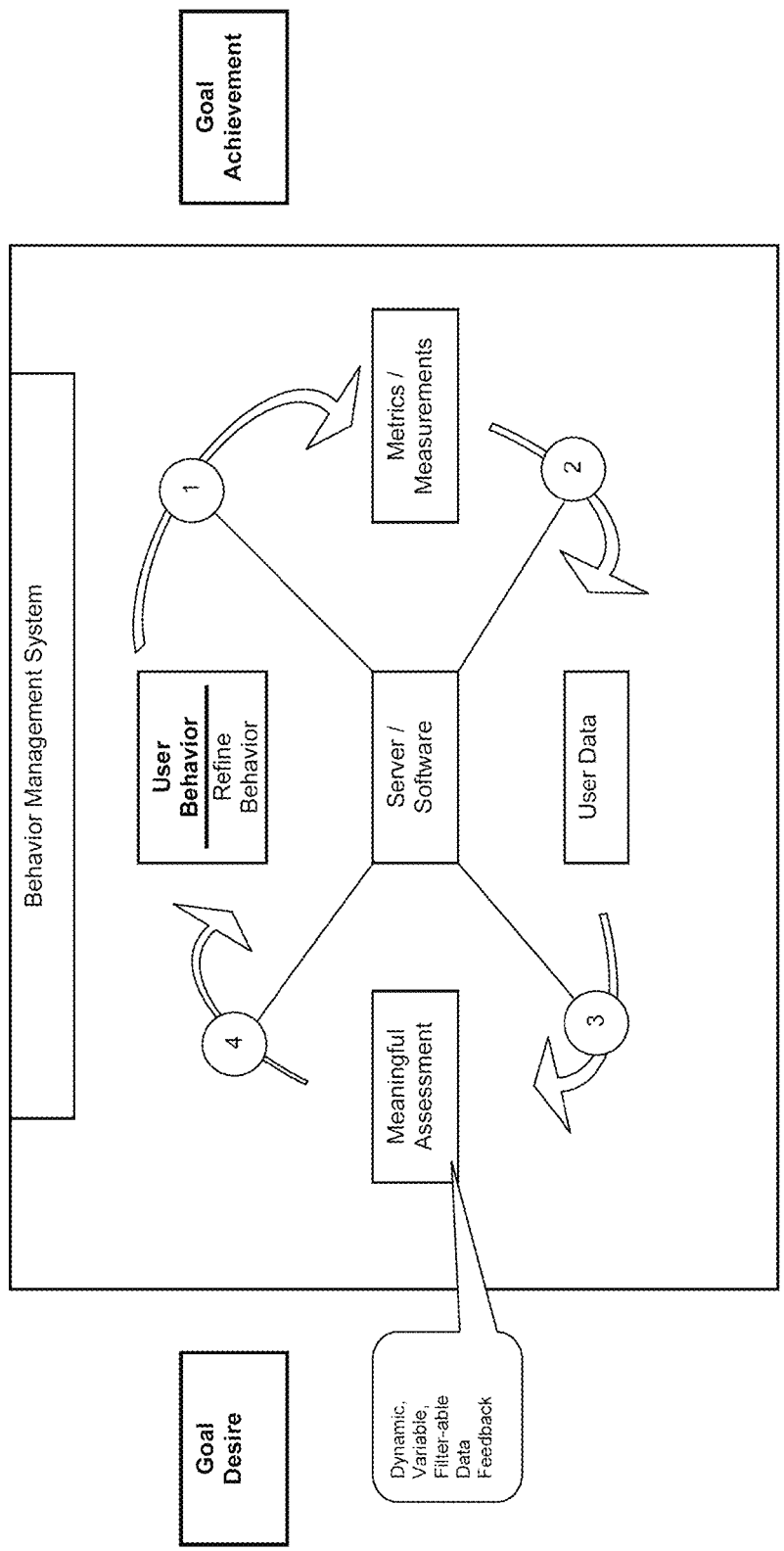
FIG. 1A shows an illustrative conceptual diagram of a behavior management system. Between a user's goal desire and goal achievement is the user's behaviors over time. A behavior management system utilizes software to define the goal and metrics to determine progress, to collect user data of these metrics including behavioral metrics, and to provide a meaningful assessment, so that the user may refine and improve behaviors. The cycle continues until the goal is achieved.

FIG. 1A illustrates the conceptual architecture of an effective hardware and software behavior management system. Between a user's goal desire and goal achievement is the user's behavior cycle. User behaviors are parsed into a set of metrics that can be measured to determine progress. User measurements, including both physical and behavioral data, with respect to these metrics are stored on servers. Data can be manually entered, captured via integrated biometric hardware devices or generated by software system processes. User data is organized to enable the display of meaningful and engaging assessment feedback. The present effective behavior management system provides assessment feedback that meets the requirements of all four effort-to-reward mechanisms—temporal, association, assimilation, and ratio—of an effective behavior management tool. A user that is properly motivated and informed refines his/her behavior and continues this cycle until the goal is achieved.

FIG. 1 diagrams the components of a hardware and software behavioral management system. Users interact with hardware, including but not limited to Internet-enabled devices, professional and consumer biometric devices with bidirectional integration and third party professional and consumer biometric devices with unidirectional integration. Such devices include, for example, body composition scales, pedometers, and heart rate monitors. These devices are connected with the system servers via a network and the behavior management software which resides there.

In one embodiment, the device comprises a body composition scale or kiosk. The fitness kiosk is a self-serve apparatus that features the following components in a powder-coated steel housing: body composition scale, internet-enabled CPU, video-enable touch screen monitor, speakers, thermal printer, an optional bill acceptor, a power supply, internet card, fuses and electrical chassis. The graphic display and auditory prompts from the speakers guide a user through a body composition test. Proprietary software, running on the CPU, integrates the scale and supporting devices from the individual control standpoint as well as in terms of the overall test sequence logic.

Test data from the kiosk is automatically sent to private user accounts online. If the local network is down for some reason, results are cached locally then uploaded when access is restored. Users can create individual accounts either on the kiosk or the website, and this, together with how the kiosk is used, is explained in more detail below.

FIG. 2 illustrates the different types of data used and generated by the system. Biometric data includes, but is not limited to, weight, body fat percentage, height, age, blood pressure readings, injury status, miles run, calories consumed, and nutritional intake. Behavioral data includes, but is not limited to, user login frequency, recording activity percentage, amount of exercise, intensity of exercise, type of exercise, and time of day meal eaten. Expression data includes, but is not limited to, expressions of opinions, preferences, feelings, moods, energy level, comments, and diary entries. Derivative data includes, but is not limited to, data derived from other types of data and/or analysis of other data, such as weight loss to date which is a subtraction of weight data from two different dates. Derivative data also includes data derived from simultaneously cross referencing various metrics. Internal system data includes, but is not limited to, data or flags linking or relating varying types of data together. Assimilated data includes, but is not limited to, data from outside databases which may or may not involve types of data mentioned. Internal process data includes, but is not limited to, obstacle and motivational type definitions, data-mining formulas, algorithms and functions. Users generate biometric, behavioral and expression data. Biometric hardware devices generate biometric and behavioral data. System software generates derivative and internal system data and utilizes internal process data.

Figure 3:
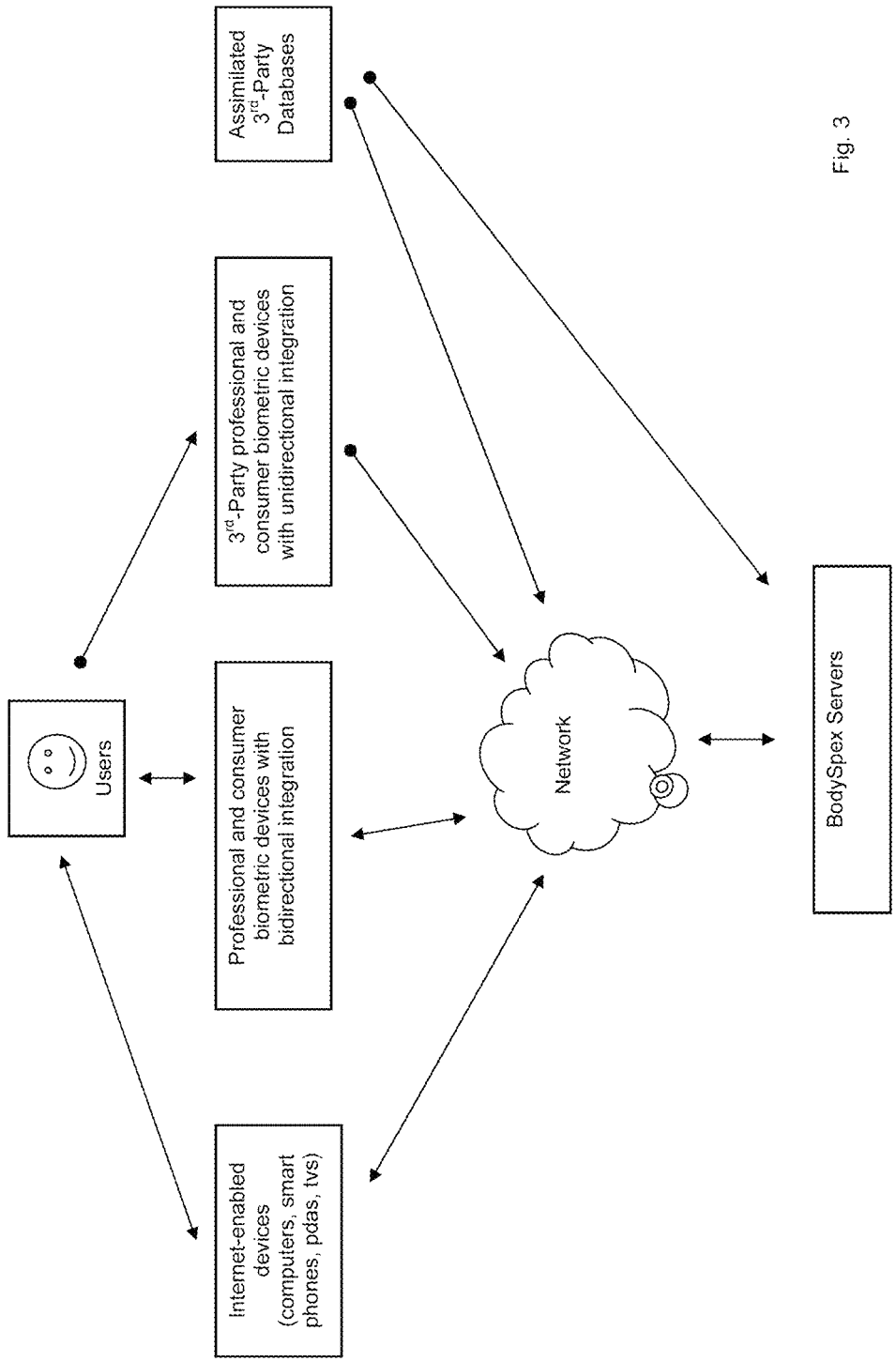
FIG. 3 shows a flow diagram of data between various components of a hardware and software behavioral management system. Data flows from and to users via Internet-enabled devices, professional and consumer biometric devices with bidirectional integration and third party professional and consumer biometric devices with unidirectional integration. Each of these data streams connects with the BodySpex servers via a network. Additional third party assimilated data flows to the servers directly or via a network.

The flow of data between the system components is shown in FIG. 3. Users enter data into the system via Internet-enabled devices, such as computers and smart phones, and via professional and consumer biometric devices with bidirectional integration, and via third party professional and consumer biometric devices with unidirectional integration. Users may receive or view data from the system via Internet-enabled devices, such as computers and smart phones, and via professional and consumer biometric devices with bidirectional integration. Internet-enabled devices and profession and consumer biometric devices with bidirectional integration send data to and receive data from the servers via a network. Third party professional and consumer biometric devices with unidirectional integration send data to the servers via a network, while assimilated third party databases send data to the servers via a network or directly.

FIG. 4 shows the system architecture. Data is organized and stored in the database. Website software is linked to the database and the website is accessed by users via a network. Web services software is linked to the database and communicates with bio-metric devices via a network.

Figure 5A:
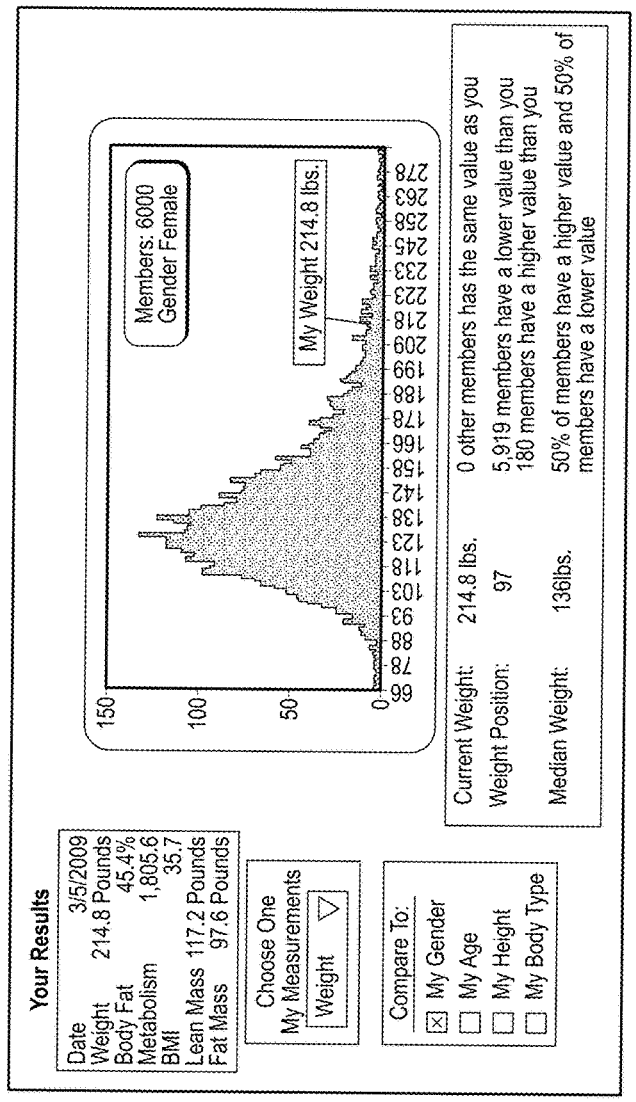
FIG. 5A shows an exemplary webpage where a user is presented with data feedback in the form of a Results Page.
Figure 5:
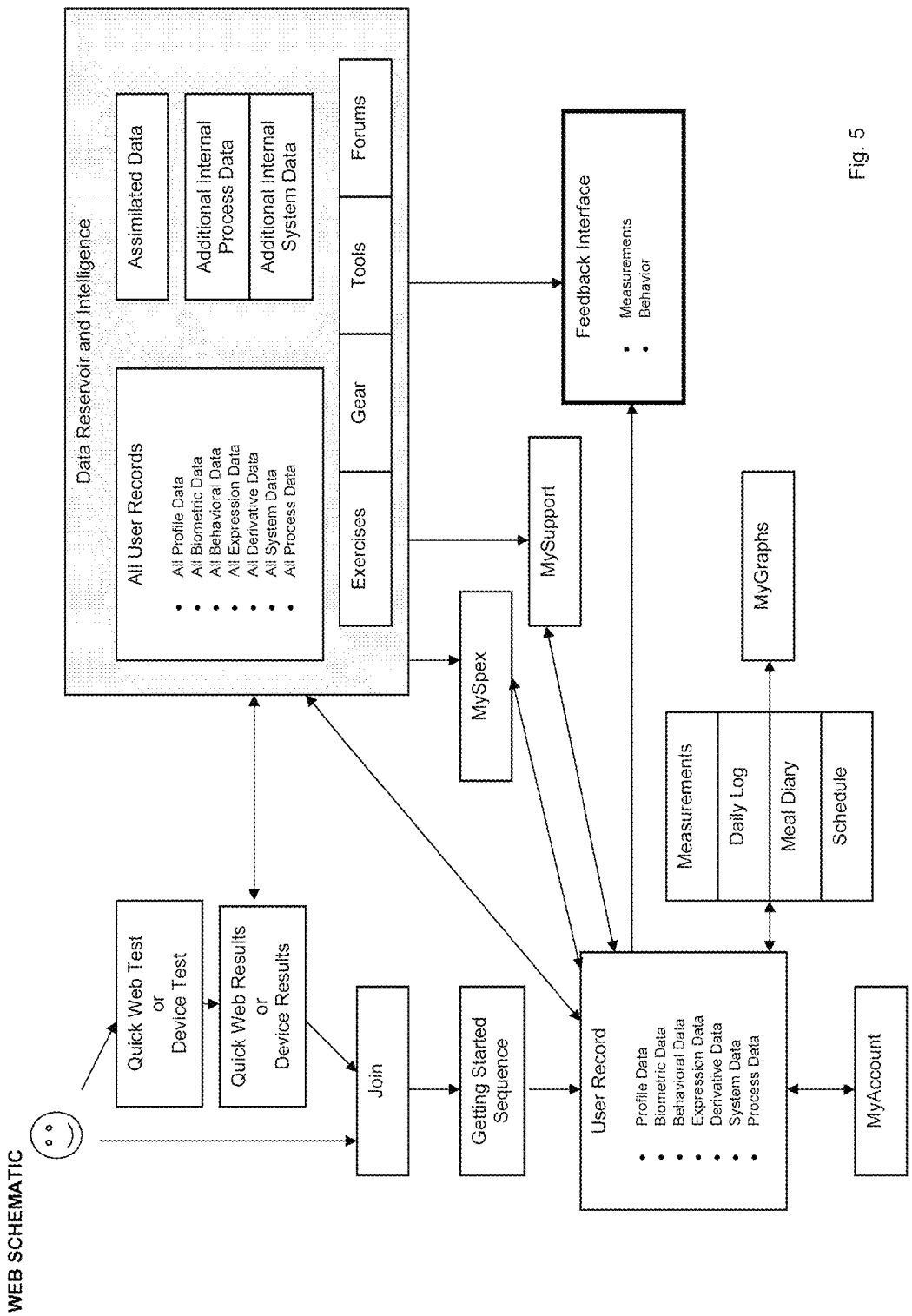
FIG. 5 shows a schematic and data flowchart for the website. Users join, and then set up their user record, optionally by completing a getting started sequence. User records are maintained and updated via various data entry screens and functions. All user record data is stored in an intelligent reservoir on the servers, where it is organized and related with other data, such as, assimilated data, internal process and system data, exercise, gear, tools, and forum data. Data is displayed for the user via their MySpex page, support features and high feedback ratio interfaces.

FIG. 5 shows a schematic and data flowchart for the website component of a hardware and software behavior management system. The design of the website clusters around three essential functions: data collection, data organization, and data display.

In general, a user's initial interaction with the system will be via the website directly or a biometric measurement test on an integrated device or system. From one of these entry points, a user is presented with data feedback in the form of a Results Page. After viewing the test results and the assessment, the user will be prompted to join. The join page is a typical website form where basic account information, such as name, gender, birth date, time zone, postal code, is gathered to create a unique user profile.

Upon validating their email address by clicking a link embedded in an automatically generated email response to their join form data, users may optionally complete a Getting Started Sequence. The Getting Started Sequence is a series of form and data collection pages to complete their User Record. In this sequence, users define a goal, including appropriate metric for measuring progress, schedule exercises, schedule nutrition and tracking items, select motivation responses, select obstacle responses, and choose support settings.

A User Record is comprised of user profile and biometric data collected as noted above, as well as other data, such as behavioral data, expression data, derivative data, system data and process data within each user's record. A User Record is regularly updated through various processes, which alter and add to the data within the User Record, including derivative data, system data and process data.

Various pages are provided for the ongoing maintenance and data entry of the user's health, fitness and lifestyle. These include measurements where periodic biometric data is recorded, as well as: Daily Log—where daily expression and behavioral data is recorded; Meal Diary—where daily expression and behavioral data is recorded; Schedule—where certain behavioral data is managed; and, MyAccount—where Profile data is managed; Challenges—where user interaction is characterized as a health and/or fitness competition, and resulting data records create an additional set of data nodes for feedback.

The present software system organizes data in a manner which enables high feedback ratio interfaces. Just as each individual User Record is stored, so too is an appropriate aggregate record of all records. A large, flexible matrix encoded with each individual User Record, as well as an aggregate record of all records, enable users to filter the reference data set and relate their specific record against a reference data set of their choice. In addition to all user records, data in the reservoir includes Assimilated Data, such as a third party database, as well as additional internal process data, additional internal system data, and exercise, gear, tools and forum databases. Each of these adds data nodes to the matrix and additional potential record relationships.

Several pages are dedicated to data display. MySpex is an overview. MySupport is a message center. MyGraphs displays a history of user data and records in numerical and/or graphic form. And the key data display feature is the high feedback ratio interfaces where users select a metric, then filter as desired to receive measurement and behavior rank and/or position assessments and other feedback.

FIG. 5A shows an exemplary Results Page. Test results, in this case showing the results of a full test from an integrated fitness kiosk (weight, body fat %, metabolism, BMI, lean mass and fat mass), are displayed with a date. A large histogram chart displays the default measurement, in this case, weight. Below the chart is useful information that shows the user's percentile in the current data set. Other information that can be provided includes (1) a Median Position, where half the users are more than and half are less than the user's position; and (2) Target positions, where results one or two positions better than the user's current position are provided.

Users can interact with their results and the feedback display. Users first select a metric. The next step is to select a data set time frame, such as, all-time, 30 days, 7 days, or today. With these selected, the system generates a chart, graph or other data display type depending on the data selection. In this case, a histogram chart of female weight is displayed with a member count on the 'y' axis and number of pounds on the 'x' axis. The chart indicates where the user is positioned for the current data set. The legend describes the current data set. Additionally, users can reference assessments or data generated through simultaneous cross referencing of multiple metrics.

A Filter Panel allows the user to filter the data set based on a pre-determined list of additional data nodes. In this example, the user can filter by gender, age, height and body type. The user can select any combination of filters. Selecting any filter alters the active reference data set and the accompanying chart responds accordingly. Altering the active reference data set affects the user's position in the data display. Position or Rank provides the user with a percentile position 1-100, which can be very motivating to the user, encouraging him or her to improve position or rank. Other valuable information that is provided can include for example, (1) a Median Position, where half the users are more and half are less than the user's position; and (2) Target positions, where results one or two positions better than the user's current position are provided.

Links to additional information can also be provided. For user's who have not fully registered on the site, there are links to join and their test data will be saved to their account.

Figure 6A:
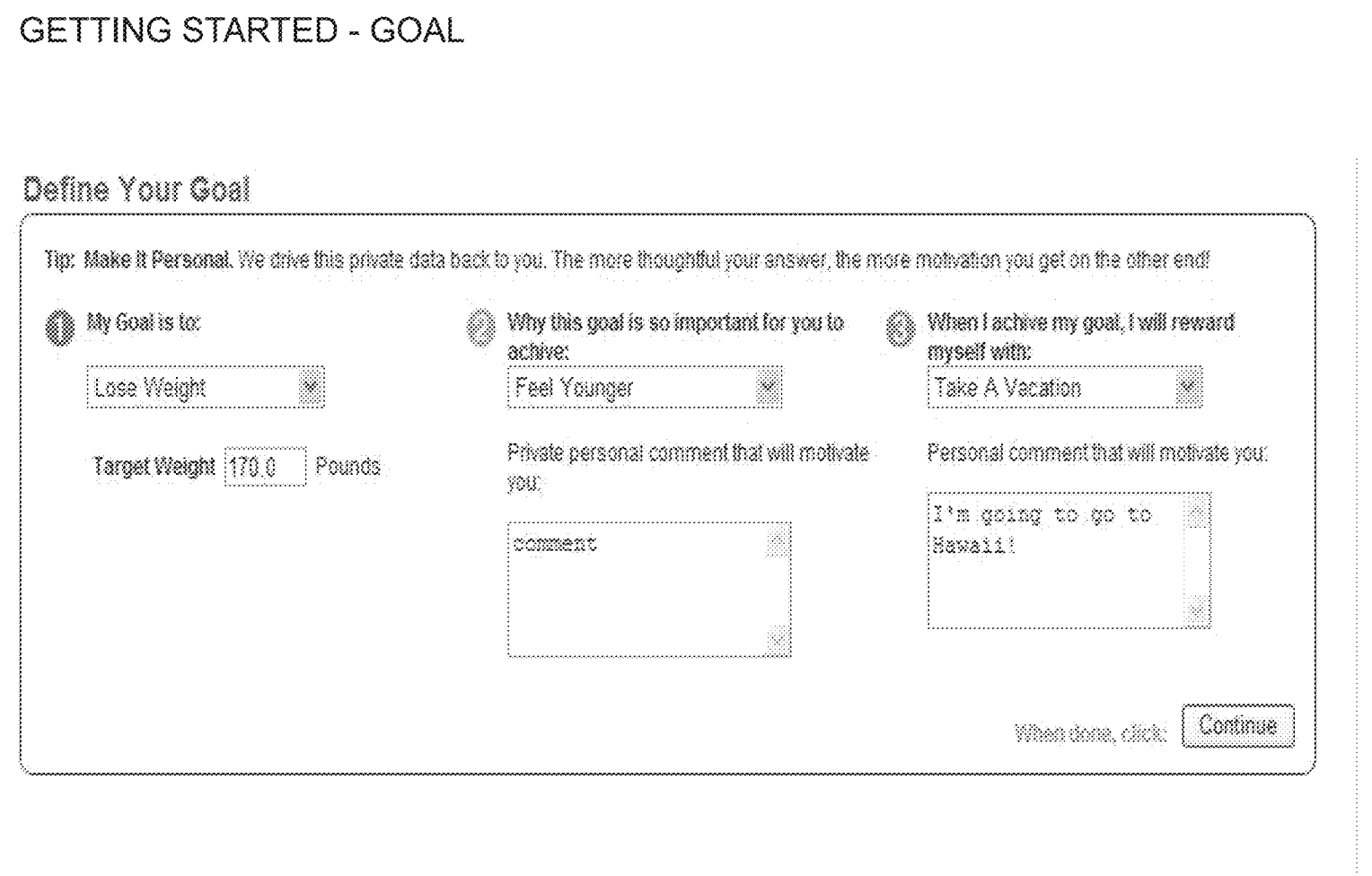

FIG. 6A shows the first stage of the Getting Started Sequence: Define Your Goal. A drop down list provides a set of pre-defined goals, such as Lose Weight or Drop Clothing Size, or an option to define your own. Upon selecting a goal, a Target Metric Field displays where the user enters their target measurement based on the type of goal selected. For example, if Lose Weight was selected, the measurement metric is pounds (or kilograms) and the user enters their Target Weight in pounds (or kilograms). Measurement metrics can be pounds, percentage, time, distance, size, inches etc., anything health, fitness, diet, or lifestyle related. For pre-defined goals, the goal and the metric data are fully integrated into the software system enabling each as a data node for feedback.

Next, a drop down list provides a set of pre-defined Goal Reasons and a comment field to enter a personalized text entry. Users may also define their own reason if the list does not suit them. For pre-defined Goal Reasons, the user's choice provides another data node. Comments are stored and can be "driven back" to the user in emails or messages upon the occurrence of certain situations to help the user stay motivated.

Next, a drop down list provides a set of pre-defined Goal Rewards and a comment field to enter a personalized text entry. Users may also define their own reward if the list does not suit them. For pre-defined Goal Rewards, the user's choice provides another data node for feedback. Comments are stored and can be "driven back" to the user in emails or messages upon the occurrence of certain situations to help the user stay motivated.

FIG. 6B shows an exemplary webpage for a user scheduling their exercise in the Getting Started Sequence. A week-long calendar view enables the user to assign their intended amount of exercise on each day of the week. This can be a repeating one-week schedule, a multi-week schedule, a monthly schedule, a daily schedule, any variation thereof, or any calendar view that is desired.

Users select whether the day of the week is a "rest" day or an "exercise" day. For each exercise day selected, the user chooses from a dropdown list how long they intend to exercise that day, i.e. 20 minutes, 45 minutes, etc. The total amount of time is calculated and displayed. Each of these choices, which days are rest or exercises, number of rest days, number of exercise days, amount of exercise on any and all days, total exercise time, etc. are additional data nodes for feedback. The exercise can be any activity that falls within the description of "exercise." Alternatively, specific exercises can be selected and scheduled rather than simply the generic "exercise." "Exercise" can be further defined in the system as a strength exercise or a cardiovascular exercise. Individually defined exercises, exercise routines, all-in-one exercise programs, etc. can also be used. Data nodes can also include such information as, for example, weight lifted, repetitions, sets, interval rest, intensity, minutes, etc.

Figure 6C:
FIG. 6C shows an exemplary webpage for a user defining their nutritional and other behavioral tracking in the getting started sequence. Users select any number of additional behaviors to track. These are additional data nodes for feedback.

FIG. 6C shows an exemplary webpage for a user defining their nutritional and other behavioral tracking in the Getting Started Sequence. Users select from a pre-defined list of items to track on a daily basis. Examples include a Meal Diary with meal names and times; calories, fat grams, protein grams, carbohydrate grams, glasses of water, hours of sleep, and treats. These items are selected via a checkbox, and are appropriately flagged as such in the User's Record. Users can use the default desired target amount of daily tracked items (for example, 8 hours of sleep, I 0 glasses of water) or define a custom amount. For pre-defined Track Items, the user's data provides another node for feedback.

FIG. 6D shows the fourth stage of the Getting Started Sequence, an exemplary webpage for a user completing their motivation profile. Users are presented with questions relating to motivation and are asked to indicate an A or B response for each question which most closely describes how they feel about the question. This feature creates sixteen distinct motivational profiles and each user is flagged for one and only one profile. This is an additional data node for feedback. The purpose is to identify and group users based on various data nodes and determine patterns and expectations based on this data to better guide and direct user's toward increased desired behaviors and goal achievement.

FIG. 6E shows the fifth stage of the Getting Started Sequence, an exemplary webpage for a user completing their obstacle profile. Users are presented with a series of checkboxes, each associated with an obstacle statement. Users indicate for each obstacle whether it has contributed to the user failing to achieve a similar goal in the past. The obstacles statements are organized in the software to form four obstacle groups: social, information, constitution, injury. This feature is organized to create sixteen distinct obstacle profiles and each user is flagged for one and only one obstacle type. This is an additional data node for feedback. The purpose is to identify and group users based on various data nodes and determine patterns and expectations based on this data to better guide and direct user's toward increased desired behaviors and goal achievement.

Figure 6F:
FIG. 6F shows an exemplary webpage for a user completing their alert and reminder settings in the getting started sequence. Users select under what circumstances they want system alert and reminder prompts via email. In addition to system logic, selections by the user are additional data nodes for feedback.

FIG. 6F shows the fifth stage of the Getting Started Sequence, an exemplary webpage for a user completing their alert and reminder settings. Users set their alert and reminders preferences via this panel. Users select checkboxes for the types of email alerts and reminders they want the software to send. In addition to system logic, selections by the user are additional data nodes for feedback.

Upon completing their Getting Started Sequence, a user is fully registered. A user's MySpex page is their private account home page, a dashboard of sorts, where their data is summarized: a calendar view summaries their upcoming scheduled activities, a summary of their position and rankings for various metrics, and a status graph of their goal progress.

FIG. 7 shows how data is organized and made accessible. All user data records are stored in the main database, and stored in a manner that allows for culling data in a variety of ways. A summary of all records that meet certain criteria are available for parsing. Users select measurement, time frame, and check filter boxes on the various Interactive Charts. This pulls up a variable dynamic (live) data set and is displayed in a variety of methods.

All measurements (1) are stored and keyed with other data that allows for filtering of that data set. Selecting a Filter (1) returns only those measurements that meet the criteria, that is, a subset of the whole initial data set. Further, selecting Filters (1 and 2) returns only those measurements that meet the criteria for 1 and 2. Users may also select only 2, for example, and the entire Measurement! (M1) data set will return a smaller data set that meets M1 and F2 criteria. In this way, any combination of filters and a measurement, and timeframe data set, is available. In this example, M1 is filtered by F1, F2, and F3, each subset of the group above.

The user's position and/or rank are determined by the user's current measurement within the active data set. As the data set is changed, the user's position will change, as will the median position/rank. Other ranks will change as well.

A projected daily routine for a user includes logging in. Then, they go to their Daily Log page to record their day's activities. Upon logging the day's activities from a pre-populated list generated by their schedule, they can review their new positions and rankings on their behavioral results page and interact with the latest data sets. A separate Meal Diary functions the same way.

Periodically, users will be prompted to their measurements page to update their measurements. Integrated devices will update this data automatically. Upon entering new data, users can review their new positions and rankings on their measurements Results Page and interact with the latest data sets.

Ideally, upon interacting with the various Results Pages, users will refine their exercise and meal schedules to move toward an ever increasing effectiveness toward reaching their goals. Users can refine their behaviors based upon the results and assessments obtained from simultaneously cross referencing various metrics within the system.

Additional behaviors that users are encouraged to participate in on the site are reading articles and comments in the public forums. They can browse an exercise library to find new exercises to incorporate into their schedule. They can receive and send support via emails and internal messaging from their friends list or group. They can join a challenge to compete with other users. They can maintain a diary, or blog. Other community features can include an events calendar for exercise and fitness events.

Figure 8:
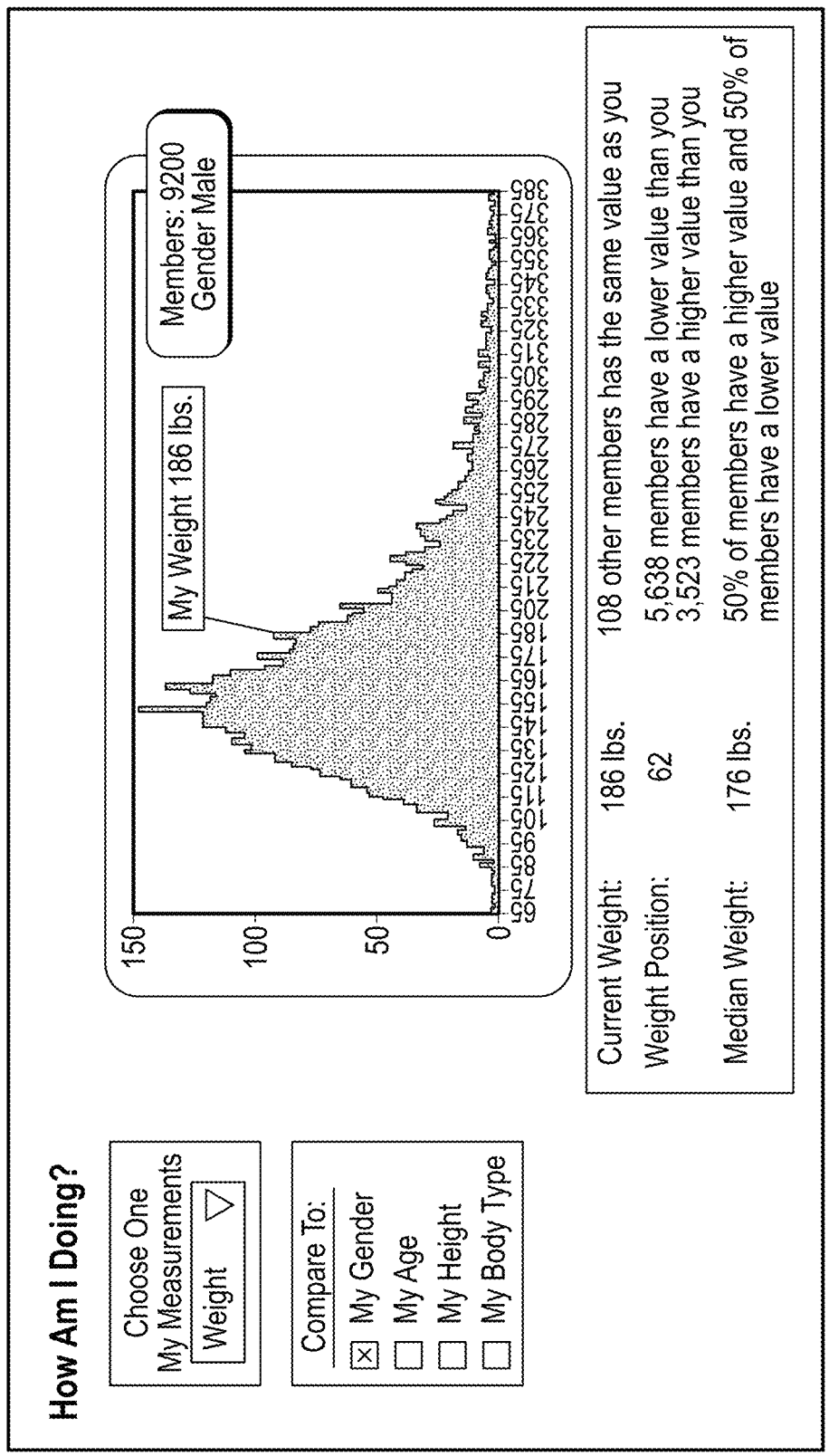
FIG. 8 shows an exemplary webpage of the high feedback ratio interface. Users select a metric, then filters as desired. A chart or graph or other data display type is automatically generated. In this case, a histogram chart of male weight is displayed with a member count on the 'y' axis and number of pounds on the 'x' axis. User rank or position, as applicable, is displayed along with other pertinent information about the active reference data set.

FIG. 8 shows an exemplary webpage of a high feedback ratio interface. Users first select a metric. The second step is to select data set time frame, such as, all-time, 30 days, 7 days, or today. With these selected, the system generates a chart, graph or other data display type depending on the data selection. In this case, a histogram chart of male weight is displayed with a member count on the 'y' axis and number of pounds on the 'x' axis. The chart indicates where the user is positioned for the current data set. The legend describes the current data set.

A Filter Panel allows the user to filter the data set based on a pre-determined list of additional data nodes. In this example, the user can filter by gender, age, and height. The user can select any combination of filters. Selecting any filter alters the active reference data set and the accompanying chart responds accordingly. Altering the active reference data set affects the user's position in the data display. Position or Rank provides the user with a percentile position 1-100, which can be very motivating to the user, encouraging him or her to improve position or rank.

Other valuable information that is provided can include (1) a Median Position, where half the users are more and half are less than the user's position; and (2) Target positions, where one or two positions better than the user's current position are provided.

The focus of the feature is to encourage the user's engagement with their measurements. They can select a data set that can more and more closely resemble their attributes. Users will "play" with the tool to see where they are and how they're doing with respect to others and determine which behavioral variations are producing the best results. Users who are thus engaged in their measurements are more inclined to improve them.

The system and methods described above fulfill four requirements of an effective behavior management tool—that is, (1) temporal, (2) tangible, (3) personally meaningful, and (4) a high feedback ratio.

EXAMPLE 1

Amy, 36 years old, joins a health club to lose fifteen pounds. She has a summer vacation planned with friends she hasn't seen in five years and wants to look good in her bathing suit. At the club, Amy notices a new BodySpex scale. The video touch screen announces free weight and body fat percentage test results, so she steps up to give it a try.

Touching the screen, Amy is presented with a Welcome screen. On this screen, Amy is offered the option of a free test, where results are emailed to the user, or a test with immediate results available for $2. Amy presses the free test button.

A Login screen appears for Amy to enter her email address or nickname, if she were already a BodySpex member. Amy taps out her email address via the onscreen keyboard. Next is a Password screen. Amy thinks of a password she can easily remember and enters it.

Amy is now presented with a screen that offers two different tests: a body fat test and a weight-only test. She notes that the body fat test must be taken in bare feet, and reads a caution that she should not have any internal electrical devices, such as a pacemaker. Determined to learn her body fat percentage, Amy selects BodyFat Test.

Amy is presented with a series of screens to collect necessary profile information for an accurate body fat test via bioelectric impedance, the underlying technology of the scale. First is a Gender screen. Amy selects the image of a woman. On the next screen, Amy enters her height, 5' 6". Amy enters her birth date: Jul. 4, 1972 on the next screen. Amy is then presented a screen with six different body types, varying from a muscular female bodybuilder to an overweight woman. Amy selects the image that most closely resembles her body type, slightly overweight. On the next screen, Amy is given the option to enter her desired weight goal. Amy uses the onscreen keypad to enter 145 lbs. Next, Amy is prompted to select an image which most closely resembles how many clothes she is wearing. Amy reads on an information popup that the scale automatically deducts the weight of clothes to get a more accurate reading. Amy selects the image in shorts and tank-top. The scale will automatically deduct 1.2 pounds from her weight.

The scale is prepared for Amy's test and Amy takes off her shoes and socks. The scale prompts Amy to step on the scale and she does. She stands still for about 15 seconds and the test is complete. The scale displays a message telling Amy to check her email for test results. The whole process has taken less than two minutes. Amy puts on her shoes and socks and does her workout.

When Amy gets home, she checks her email. There is an email from BodySpex with a few kind words and a link to her results. Amy clicks the link in her email. Embedded into this link is a unique identifier, enabling the BodySpex system to display Amy's results specifically and privately for her.

A browser is opened and Amy is automatically directed to the scale results page on the BodySpex website where she can read her test results: Weight 160 lbs., BodyFat 33.1%, Metabolism 1245 kcals, BMI 26.3, Lean Mass 107 lbs, Fat Mass 53 lbs.

In addition to her results, and what really catches Amy's eye, is an interactive feedback Chart. Right now the Chart is showing a graph of a lopsided bell curve with a little flag indicating her current weight of 160 lbs. The Chart legend reads Members 9,856 and Gender: Female. Below the Chart is more information. It indicates her Weight position is 57 and that 5,617 members have a lower value while 4,238 members have a higher value. Amy is in the 57th percentile for this reference group.

Amy sees a drop down list that currently reads 'weight', but has options for all of the metrics provided by the BodySpex scale test: weight, bodyfat %, metabolism, BMI, LeanMass, and FatMass. Below this is a series of check boxes under a title that reads "Compare To". The checkbox for My Gender is checked. Others, like My Age, My Height are not checked. Amy checks the box for My Age.

The chart immediately changes to reflect a new active reference data. The chart legend now reads Members: 1,234, Gender Female, Age 35-37. Amy's position on the chart has changed and so has her position information below the chart. Her rank for this data reference set has improved to 48. Amy rightly concludes that for women her age, she's better than the median.

Excited to see how she measures up against all the possible variables offered with this chart and her one test, she spends ten minutes selecting each of the metrics and each combination of filters for each.

Amy discovers there are 100 members who match her profile closely: Female, 35-37 years old, 5'5"-5'7' tall, and workout at her club. Amy's ranked 51 and that doesn't sit well with her. She's highly motivated to get in the top 25, and can't wait to get back to the gym.

Amy notes that becoming a BodySpex.com member is free and members enjoy many more metrics and filters on their interactive feedback charts. Amy promptly clicks the join button, where her scale data will be automatically imported to her new web account. Amy plans to take another scale test at her club in a week.

It is to be recognized that depending on the embodiment, certain acts or events of any of the methods described herein can be performed in a different sequence, may be added, merged, or left out all together (e.g., not all described acts or events are necessary for the practice of the method). Moreover, in certain embodiments, acts or events may be performed concurrently, e.g., through multi-threaded processing, interrupt processing, or multiple processors, rather than sequentially.

Those of skill in the art will recognize that the various illustrative logical blocks and algorithm steps described in connection with the embodiments disclosed herein may be implemented as electronic hardware, software stored on a computer readable medium and executable by a processor, or combinations of both. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present invention.

The various illustrative logical blocks, modules, and circuits described in connection with the embodiments disclosed herein may be implemented or performed with a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general purpose processor may be a microprocessor, but in the alternative, the processor may be any conventional processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration.

The steps of a method or algorithm described in connection with the embodiments disclosed herein may be embodied directly in hardware, in a software module executed by a processor, or in a combination of the two. A software module may reside in RAM memory, flash memory, ROM memory, EPROM memory, EEPROM memory, registers, hard disk, a removable disk, a CD-ROM, or any other form of storage medium known in the art. An exemplary storage medium is coupled to the processor such the processor can read information from, and write information to, the storage medium. In the alternative, the storage medium may be integral to the processor. The processor and the storage medium may reside in an ASIC.

Various modifications to these examples may be readily apparent to those skilled in the art, and the principles defined herein may be applied to other examples without departing from the spirit or scope of the novel aspects described herein. Thus, the scope of the disclosure is not intended to be limited to the examples shown herein but is to be accorded the widest scope consistent with the principles and novel features disclosed herein.

What is claimed is:

1. A behavioral management system comprising:
   a biometric hardware device selected from the group consisting of a body weight scale, a body composition scale, a pedometer and a heart rate monitor, wherein the biometric hardware device generates user generated data and wherein the user generated data is stored in a database via a network; and
   behavior management software connected to the database, wherein user generated data is stored in and/or accessed from the database in a manner that enables interfaces that allow a user of the biometric hardware device to reference a data set containing data related to at least one metric for each of a set of other behavior management software users, wherein the other users are individuals who can be connected to the database via other biometric hardware devices and the network, the referenced data set being actively defined based on data flows from a plurality of users to the database via biometric hardware devices and the network, and further allows the user to interact with the behavior management software to select from one or more filters to generate a filtered data subset of the referenced data set, the filtered data subset being based on the selection, such that the user is provided with one or more changeable positions and/or ranks, each of the changeable positions and/or ranks being based on a comparison of a value of a metric of the user generated data with values of the respective metric of the filtered data subset; and
   wherein the one or more filters comprises at least one of gender, age, height, body type, time zone, or postal code.

2. The system of claim 1, wherein the user generated data comprises at least one of weight, body fat percentage, body mass index, miles run, heart rate, amount of exercise, intensity of exercise, type of exercise, hours of sleep, lean mass, fat mass, or metabolism.

3. The system of claim 1, wherein results for individuals one or more positions different from the user's current position in a user selected group are provided.

4. The system of claim 1, wherein users are provided metric data from users one or more positions different from the user's current position in a user selected group.

5. The system of claim 1, wherein multiple types of data are related to determine a pattern.

6. The system of claim 1, wherein cross referencing multiple metrics generate expectations for the user within the user selected group.

7. The system of claim 1, wherein behavioral variations across multiple metrics that produce better results are flagged.

8. The system of claim 1, wherein behavioral variations across multiple metrics that produce poorer results are flagged.

9. The system of claim 1, wherein users can assess the flagged behavioral variations within the user selected group.

10. The system of claim 1, wherein the user generated data further comprises expression data comprising at least one of opinions, preferences, feelings, moods, or energy level.

11. The system of claim 1, wherein the user generated data further comprises user defined goals comprising target measurement metrics and wherein, the target measurement metrics comprises at least one of weight, percentage, time, distance, size, inches, or other health, fitness, diet and lifestyle related measurement metrics.

12. The system of claim 1, wherein the user generated data further comprises obstacles that have contributed to the user failing to achieve a goal in the past.

13. The system of claim 12, wherein the obstacles are organized into four obstacle groups: social, information, constitution, injury; and wherein the four obstacle groups are organized to create additional distinct obstacle profiles.

14. The system of claim 13, wherein the obstacle profiles comprise additional data nodes for feedback used to identify and group users; and wherein patterns and expectations based on this data are used to guide and direct users toward increased desired behaviors and goal achievement.

15. The system of claim 1, wherein the user generated data further comprises user responses to motivation related questions and wherein the user responses are used to generate distinct motivational profiles.

16. The system of claim 15, wherein the motivational profiles comprise additional data nodes for feedback used to identify and group users; and wherein patterns and expectations based on this data are used to guide and direct users toward increased desired behaviors and goal achievement.

17. The system of claim 1, wherein the user generated data further comprises user defined nutritional and behavior data comprising time of day meal eaten, calories, fat grams, protein grams, carbohydrate grams, glasses of water, nutritional intake, or treats.

* * * * *

(12) INTER PARTES REVIEW CERTIFICATE (2736th)
United States Patent (10) Number: US 9,757,066 K1
McGilvery et al. (45) Certificate Issued: Jul. 8, 2022

(54) METRICS ASSESSMENT SYSTEM FOR HEALTH, FITNESS AND LIFESTYLE BEHAVIORAL MANAGEMENT

(71) Applicants: Justin McGilvery; Dale E. Mitbo

(72) Inventors: Justin McGilvery; Dale E. Mitbo

(73) Assignee: FAT STATZ LLC

Trial Number:

IPR2020-01665 filed Oct. 1, 2020

Inter Partes Review Certificate for:

Patent No.: 9,757,066
Issued: Sep. 12, 2017
Appl. No.: 15/401,922
Filed: Jan. 9, 2017

The results of IPR2020-01665 are reflected in this inter partes review certificate under 35 U.S.C. 318(b).

INTER PARTES REVIEW CERTIFICATE
U.S. Patent 9,757,066 K1
Trial No. IPR2020-01665
Certificate Issued Jul. 8, 2022

AS A RESULT OF THE INTER PARTES REVIEW PROCEEDING, IT HAS BEEN DETERMINED THAT:

Claims 1-4 and 11 are cancelled.

\* \* \* \* \*